US005987359A

United States Patent [19]
Freed et al.

[11] Patent Number: 5,987,359
[45] Date of Patent: *Nov. 16, 1999

[54] METHOD FOR TREATING DYSPHAGIA WITH ELECTRICAL STIMULATION

[75] Inventors: Marcy L. Freed, Pepper Pike, Ohio; Leonard A. Freed, Kailua, Hi.; Michael O. Christian, Beachwood, Ohio; Howard Tucker, Cleveland Heights, Ohio; Bernard Kotton; Erol M. Beytas, both of Beachwood, Ohio; Marie Asmar, Richmond Heights, Ohio

[73] Assignee: ESD Limited Liability Co., Beachwood, Ohio

[*] Notice: This patent is subject to a terminal disclaimer.

[21] Appl. No.: 08/956,448

[22] Filed: Oct. 23, 1997

Related U.S. Application Data

[63] Continuation of application No. 08/549,046, Oct. 27, 1995, Pat. No. 5,725,564.

[51] Int. Cl.$^6$ .................................................. A61N 1/18
[52] U.S. Cl. .............................................. 607/72
[58] Field of Search .................................. 607/63, 72, 39, 607/40, 62, 118

[56] References Cited

U.S. PATENT DOCUMENTS

| | | | |
|---|---|---|---|
| 4,167,190 | 9/1979 | Sorenson et al. | 607/72 |
| 4,411,268 | 10/1983 | Cox . | |
| 4,505,275 | 3/1985 | Chen . | |
| 4,519,400 | 5/1985 | Brenman et al. . | |
| 4,690,145 | 9/1987 | King-smith et al. | 607/72 |
| 4,827,935 | 5/1989 | Geddes et al. . | |
| 4,830,008 | 5/1989 | Meer . | |
| 4,907,602 | 3/1990 | Sanders . | |
| 5,016,647 | 5/1991 | Sanders . | |
| 5,133,354 | 7/1992 | Kallok . | |
| 5,423,869 | 6/1995 | Poore et al. . | |

FOREIGN PATENT DOCUMENTS

| | | |
|---|---|---|
| 0036742 | 9/1981 | European Pat. Off. . |
| 0404427 | 12/1990 | European Pat. Off. . |
| WO 93/06559 | 4/1993 | WIPO . |
| WO 9318820 | 9/1993 | WIPO . |

OTHER PUBLICATIONS

George L. Larsen, Ph.D., "Conservative Management for Incomplete Dysphagia Paralytica," Arch Phys Med Rehabil vol. 54, pp. 180–185 Apr. 1973.

Robert M. Miller, PhD & Michael E. Groher, PhD, "Speech–Language Pathology and Dysphagia: A Brief Historical Perspective," Dysphagia 8:180–184 (1993).

H. Miki, W. Hida, T. Chonan, Y. Kikuchi, and T. Takishima, "Effects of Submental Electrical Stimulation During Sleep on Upper Airway Patency in Patients With Obstructive Sleep Apnea," American Review of Respiratory Disease, vol. 140, No. 5, pp. 1285–1289 (1989).

(List continued on next page.)

*Primary Examiner*—Scott M. Getzow
*Attorney, Agent, or Firm*—Covington & Burling

[57] ABSTRACT

This invention is directed to a simple, non-invasive method and device for treating dysphagia and artificially promoting swallowing by electrical stimulus. In the present invention, a plurality of electrodes are selectively placed in electrical contact with tissue of a pharyngeal region of patient and a series of electrical pulses in electrical contact with each of the plurality of electrodes with a generator. The generator includes a pulse rate modulator for generating each of the electrical pulses having a frequency generally fixed at 80 hertz, a pulse width modulator for generating each pulse of the series of electrical pulses at a duration generally fixed at 300 microseconds, and a governor for regulating the electrical pulses such that at least one of current so as not to exceed 4.4 milliamps RMS or power so as not to exceed 9.6 MW RMS. The electrical pulses selectively stimulate muscles located proximate to the selectively placed electrodes to initiate swallowing.

1 Claim, 5 Drawing Sheets

OTHER PUBLICATIONS

Pamela S. Henderson, MD; James I. Cohen, MD. PhD; Per–Olaf Jarnberg, MD, PhD,; James D. Smith, MD; Wendell Stevens, MD. "A Canine Model For Studying Laryngospasm And Its Prevention," Laryngoscope 102, pp. 1237–1241, Nov. 1992.

Masafumi Suzuki, MD; Clarence T. Sasaki, MD. "Laryngeal Spasm: A Neurophysiologic Redefinition," Ann. Otol. 86, pp. 150–157, 1977.

Clarence T. Sasaki, MD; Masafumi Suzuki, MD. "Laryngeal Reflexes in Cat, Dog, and Man," Arch Otolaryngol vol. 102, pp. 400–402, Jul. 1976.

Database WPI, Section PQ, Week 9235, Derwent Publications Ltd., London; Class P34, An 92–291537 XP002090877 & SU 1 683 744A (A Med Neurology Res Inst), Oct. 15, 1991; abstract.

METHOD FOR TREATING DYSPHAGIA WITH ELECTRICAL STIMULATION

This application is a continuation of Ser. No. 08/549,046, filed Oct. 27, 1995, now U.S. Pat. No. 5,725,564.

BACKGROUND OF THE INVENTION

This invention relates to a method and device for effectively treating dysphagia. In particular, the present invention relates to a method and device for treating dysphagia by providing electrical stimulation to the pharyngeal region of an associated animal.

Dysphagia is the inability to swallow or difficulty in swallowing and may be caused by stroke, neurodegenerative diseases, or respiratory disorders. Swallowing is a complicated action which is usually initiated voluntarily but always completed reflexively, whereby food is moved from the mouth through the pharynx and esophagus to the stomach. The act of swallowing occurs in three stages and requires the integrated action of the respiratory center and motor functions of multiple cranial nerves, and the coordination of the autonomic system within the esophagus.

In the first stage, food is placed on the surface of the tongue. The tip of the tongue is placed against the hard palate. Elevation of the larynx and backward movement of the tongue forces the food through the isthmus of the fauces in the pharynx. In the second stage, the food passes through the pharynx. This involves constriction of the walls of the pharynx, backward bending of the epiglottis, and an upward and forward movement of the larynx and trachea. Food is kept from entering the nasal cavity by elevation of the soft palate and from entering the larynx by closure of the glottis and backward inclination of the epiglottis. During this stage, respiratory movements are inhibited by reflex. In the third stage, food moves down the esophagus and into the stomach. This movement is accomplished by momentum from the second stage, peristaltic contractions, and gravity. Although the main function of swallowing is the propulsion of food from the mouth into the stomach, swallowing also serves as a protective reflex for the upper respiratory tract by removing particles trapped in the nasopharyrix and oropharynx, returning materials refluxed from the stomach into the pharynx, or removing particles propelled from the upper respiratory tract into the pharynx. Therefore, the absence of adequate swallowing reflex greatly increases the chance of pulmonary aspiration.

In the past, patients suffering from dysphagia have undergone dietary changes or thermal stimulation treatment to regain adequate swallowing reflexes. Thermal stimulation involves immersing a mirror or probe in ice or cold substance. The tonsillar fossa is stimulated with the mirror or probe and the patient closes his mouth and attempts to swallow. While these traditional methods are usually effective for treating dysphagia, these methods often require that the patient endure weeks or months of therapy.

Electrical stimulation has often been used as a method for alleviating pain, stimulating nerves, and as a means for diagnosing disorders of the spinal cord or peripheral nervous system. Electrical stimulation has further been used to facilitate muscle reeducation and with other physical therapy treatments. In the past, electrical stimulation was not recommended for use in the neck or thoracic region as severe spasms of the laryngeal and pharyngeal muscles may occur resulting in closure of the airway or difficulty in breathing. Further, the introduction of electrical current into the heart may cause cardiac arrhythmia. Electrical stimulation has been used to stimulate the recurrent laryngeal nerve to stimulate the laryngeal muscles to control the opening of the vocal cords to overcome vocal cord paralysis, to assist with the assessment of vocal cord function, to aid with intubation, and other related uses. However, heretofore, electrical stimulation has not been used in the treatment of dysphagia to promote the swallowing reflex which involves the integrated action of the respiratory center and motor functions of multiple cranial nerves, and the coordination of the autonomic system within the esophagus.

It is desirable to have a simple, non-invasive method and device for treating dysphagia and artificially promoting swallowing.

SUMMARY OF THE INVENTION

In accordance with the present invention, there is provided a simple, non-invasive method and device for treating dysphagia and artificially promoting swallowing, wherein electrical stimulus is provided to the pharyngeal region of a patient to stimulate muscles located in the pharyngeal region in order to promote swallowing.

In accordance with the present invention, there is provided a simple, non-invasive method for treating dysphagia and artificially promoting swallowing by electrical stimulus, the method comprising selectively placing electrodes in electrical contact with tissue of a pharyngeal region of patient and generating a series of electrical pulses in electrical contact with each of the plurality of electrodes, wherein the electrodes deliver a series of electrical pulses to selectively stimulate muscles located proximate to the selectively placed electrodes to initiate swallowing.

In accordance with the present invention, there is provided a simple, non-invasive device for treating dysphagia and artificially promoting swallowing, the device comprising a plurality of electrodes adapted to be selectively placed in electrical contact with tissue of a pharyngeal region of a patient and a generator for generating a series of electrical pulses in electrical contact with each of the plurality of electrodes, the generator comprising a pulse rate modulator for generating each of the electrical pulses having a frequency generally fixed at 80 hertz, a pulse width modulator for generating each pulse of the series of electrical pulses at a duration generally fixed at 300 microseconds, and a governor for regulating the electrical pulses such that at least one of the current so as not to exceed 4.4 milliamps RMS or power so as not to exceed 9.6 MW RMS.

These and other aspects of the invention will be apparent to those skilled in the art upon reading and understanding the specification that follows.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein.

DETAILED DESCRIPTION OF THE PREFERRED EMBODIMENTS

Figure 1:
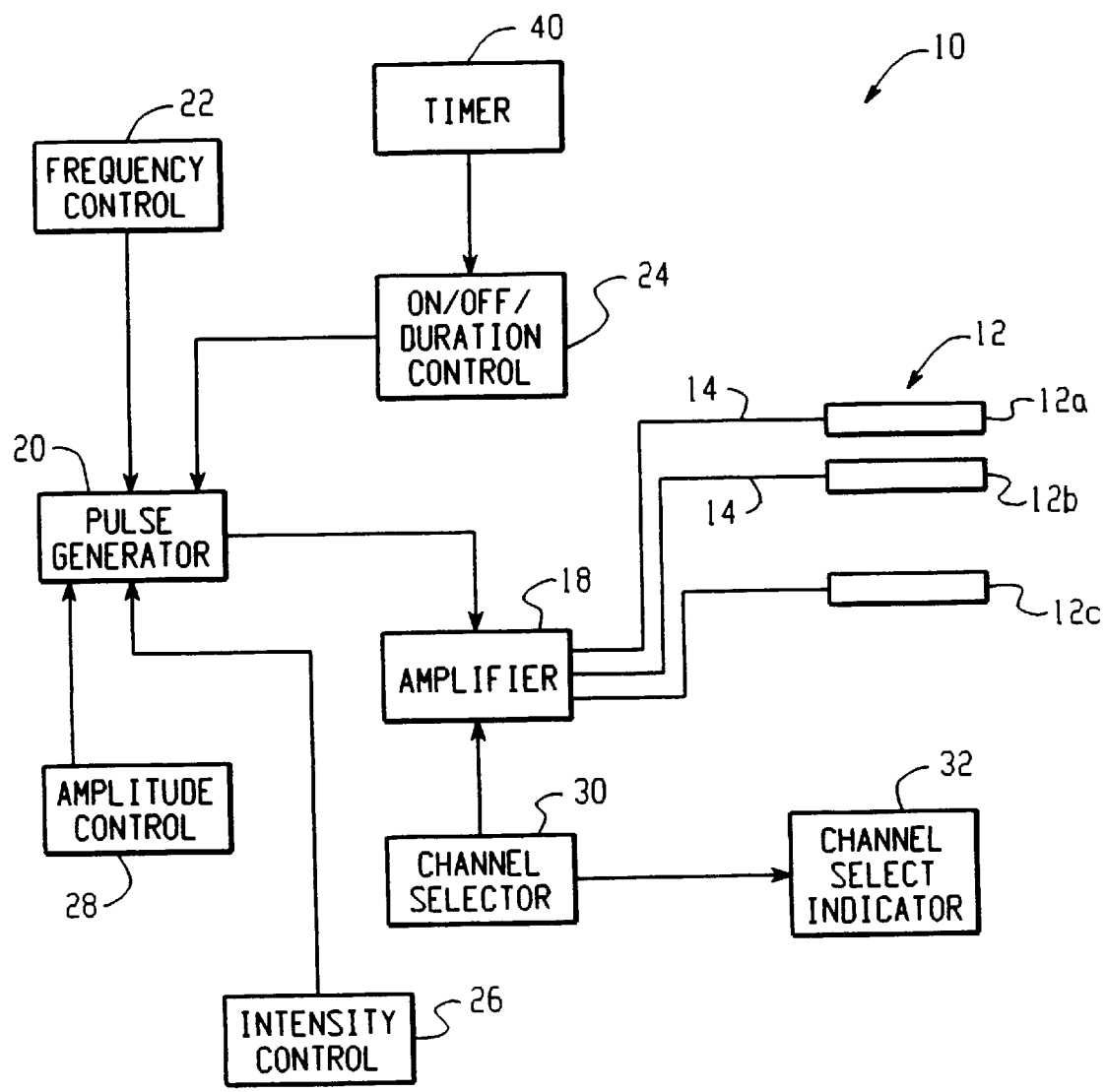
FIG. 1 is a simplified fragmentary illustration of an electrical pharyngeal neuromuscular stimulator for use in promoting swallowing according to the present invention.

This invention is directed to a simple, non-invasive method and device for electrical pharyngeal neuromuscular stimulation for artificially promoting swallowingwherein electrical stimulus is provided to the pharyngeal region of a patient to stimulate muscles located in the pharyngeal region in order to promote swallowing. Referring now to the drawings wherein the showings are for the purposes of illustrating the preferred embodiment of the invention only and not for purposes of limiting same, the electrical pharyngeal neuromuscular stimulation device 10 as shown in FIG. 1 is comprised of a plurality of electrodes 12 adapted to be selectively placed in electrical contact with tissue of a pharyngeal region of a patient and a generator 20 for generating a series of electrical pulses in electrical contact with each of the plurality of electrodes.

The device 10 is preferably comprised of two electrodes. The electrodes 22 are preferably made of metal or some other physiologically acceptable conductive material. In general, the electrodes 12 are suitably any conventional and convenient shape which is suited for physiological applications. Lead wires 14 are attached to each electrode and are suitable for attachment to the generator 20. The lead wires 14 are made from any physiologically acceptable conductive metal, preferably insulated aluminum wire.

The subject wave forms are suitably realized by selective control of a pulse generator working in connection with an amplifier 18. The generator 20 is comprised of a pulse rate modulator or a frequency controller 22 for generating each of the electrical pulses having a frequency generally fixed at 80 hertz. The generator 20 is also comprised of a pulse width modulator suitably accomplished by an on/off/duration control 24 for generating each pulse of the series of electrical pulses at a duration generally fixed at 300 microseconds. The generator is further comprised of a governor 26 for regulating the electrical pulses such that the electrical current does not exceed 4.4 milliamps RMS, the power does not exceed 9.6 MW RMS, or both. The current applied will vary depending on the physical condition and tolerance of the patient but the current applied should be sufficient to produce the desired response and promote the swallowing reflex. The intensity of the current is increased by small increments until the tolerance and comfort level limits are reached in the patient. However, the current which is applied must not be too intense and therefore, result in laryngeal spasms or cardiac arrhythmia in the patient. Another input to pulse generator 20 is formed from amplitude control module 28. The amplitude control module 28 allows for selective control of an amplitude of pulses generated from pulse generator 20. The channel selector 30 suitably forms another input to amplifier 18 to allow for concurrent activation of sets of electrodes 12. The status of channel selector is advantageously indicated by channel selector indicator 32.

In one embodiment of the present invention, the generator continuously generates electrical pulses for a predetermined period of time. Preferably, electric pulses are continuously generated and delivered to the electrodes until a complete swallow is achieved or the tolerance level is reached in the patient. Additional treatments wherein the generator continuously generates electric pulses are suitably performed on the patient as necessary.

In another embodiment of the present invention, the generator selectively generates cycles of electrical pulses. The generator is further comprised of a treatment time controller which is also suitably accomplished with the control 26 real time information which is provided by a timer 40. The timer 40, control 26, and pulse generator 16 also serve to provide functions of a treatment off-time controller, an on-ramp controller, and an off-ramp controller Treatment time control selectively controls the duration of time wherein the generator selectively generates cycles of electric pulses. The treatment time is any suitable period, such as fifteen, thirty, or sixty minutes. As with all settings, the particular values are highly application and patient specific. Thus, a suitable duration of the electric pulses in each cycle is set. Preferably, the duration of electric pulses in each cycle is the range of about 0.5 seconds to about 30 seconds. A selection is made for an amount of time between each cycle. Preferably, the amount of time between cycles is from about 0.1 seconds to about 60 seconds. A selection is also made for the amount of time required to reach the maximum intensity in each cycle. Preferably, the amount of time required to reach the maximum intensity is between about 0.1 seconds to about 6.0 seconds. A selection is further made for the amount of time required to decrease from the maximum intensity to zero intensity at the end of each cycle. Preferably, the amount of time required to decrease from the maximum intensity to zero intensity is between about 0.1 seconds to about 6.0 seconds. A suitable commercially available device which provides the functions described above is found in the Staodyn® EMS+2 System manufactured by Staodyn, Inc. and described in the associated instruction manual which is herein incorporated by reference.

Figure 2:
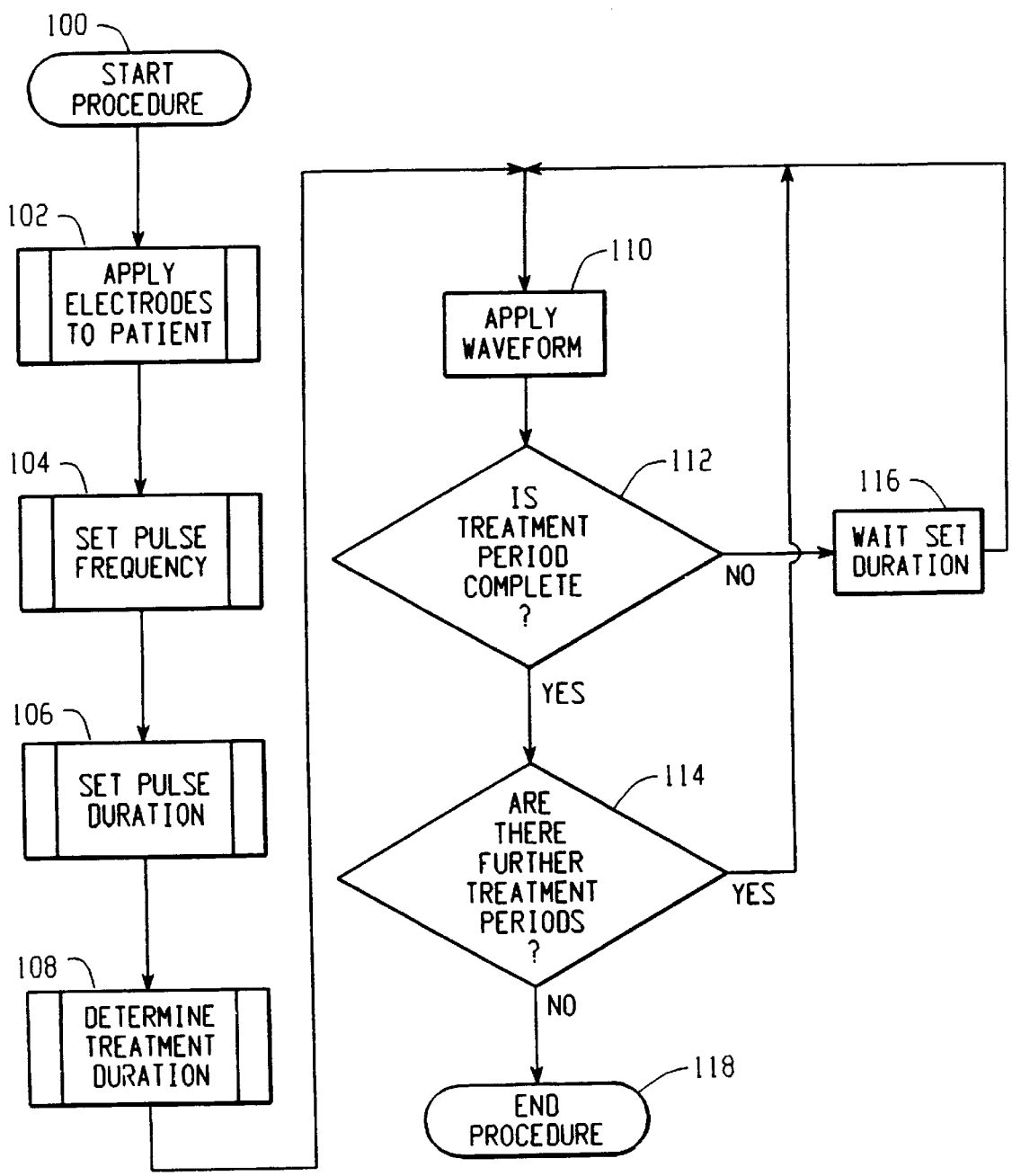
FIG. 2 is a flow chart of a method for electrical pharyngeal neuromuscular stimulation for promoting swallowing according to the present invention.

FIG. 2 provides a flow chart of the method for electrical pharyngeal neuromuscular stimulation for promoting swallowing according to the present invention. Turning to block 100, the procedure for treating dysphagia with electrical stimulation is commenced. Next, at block 102, actual electrodes are applied to the pharyngeal area of a patient. The particulars for electrode placement and selection have been disclosed elsewhere in the subject application.

Turning next to block 104, a pulse frequency is set in accordance with the parameters disclosed above. Similarly, at block 102, pulse duration is set. Finally, at block 108, a determination of a treatment duration is made, as well as to the number of treatment periods which are to be applied.

Turning next to block 110, an actual waveform associated with the previously selected parameters is applied to the pharyngeal area of a patient. Next, at block 112, a determination is made as to whether a treatment period has been completed in accordance with the preselected standards. A positive determination causes progress to decision block 114 and a negative determination causes progress to block 116. At block 116, a set duration is applied as a wait period for which progress is returned to block 110, as described above.

At block 114, a determination is made as to whether there are further treatment periods merited. A positive determination causes a return to block 110. Negative determination signals completion of the treatment procedure and progress to termination block 118.

Figure 3:
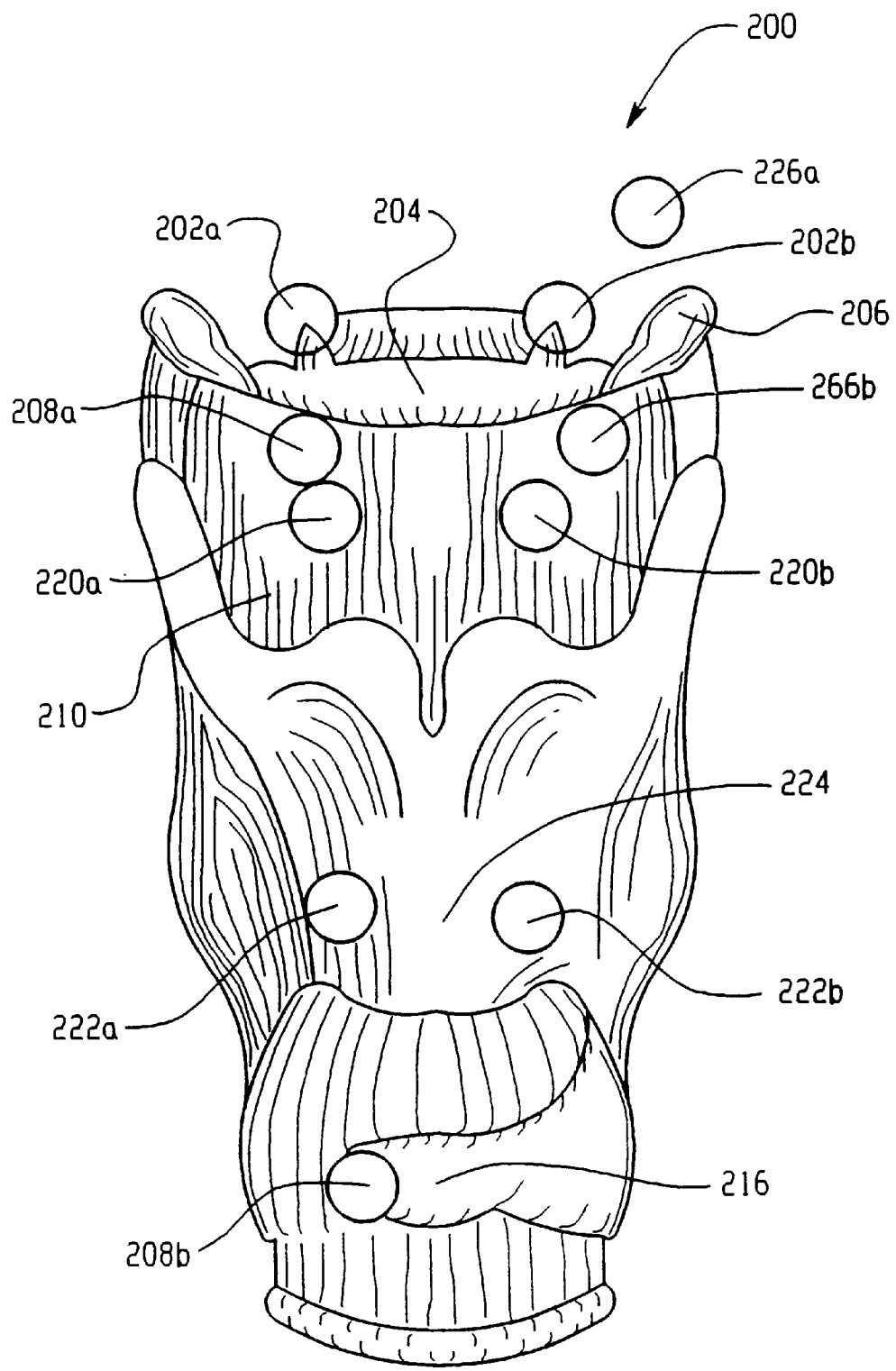
FIG. 3 is a view of a portion a pharyngeal region of a patient illustrating placement of electrodes according to the present invention.
Figure 4:
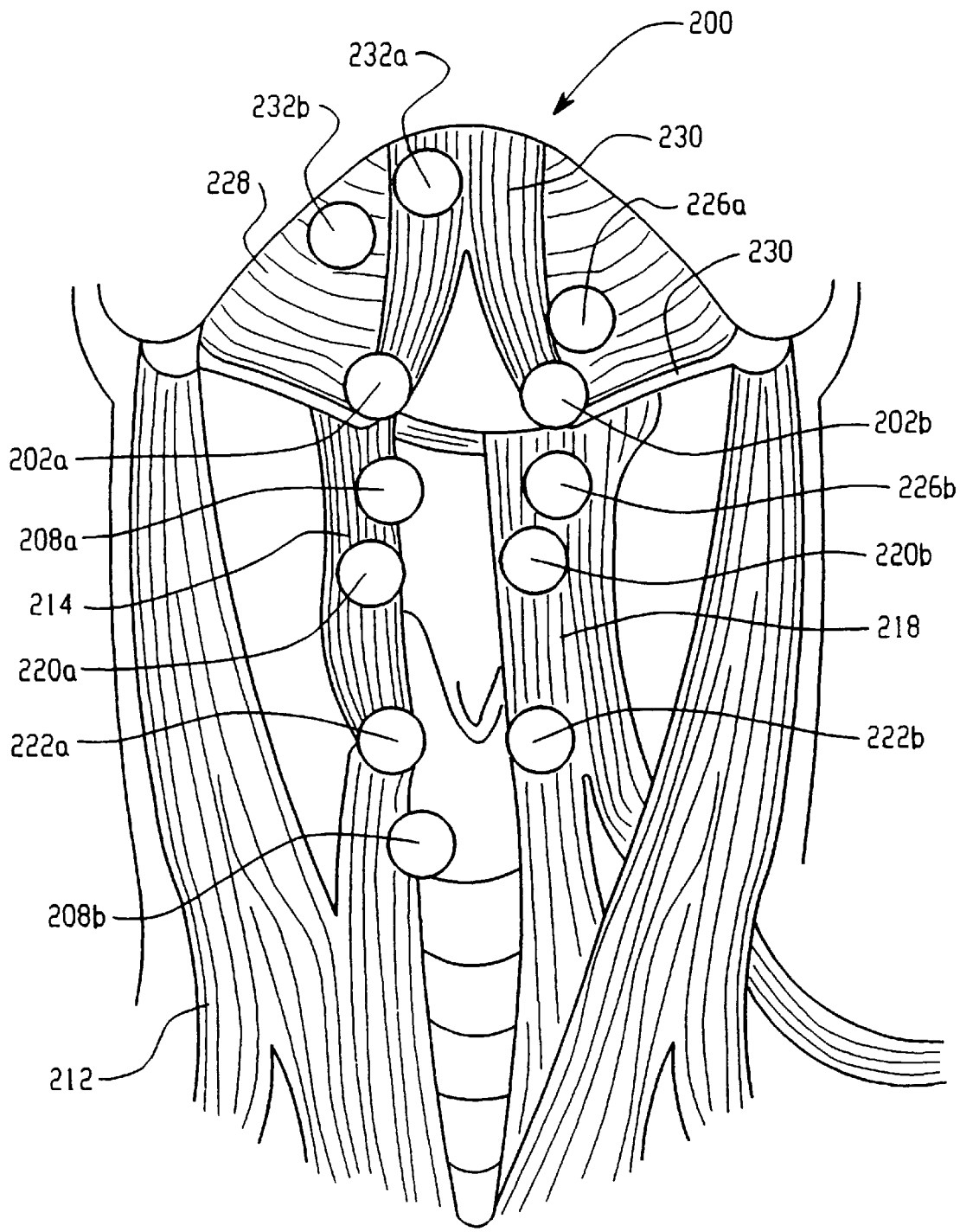
FIG. 4 is a view of a portion a pharyngeal region of a patient illustrating placement of electrodes according to the present invention.

The electrodes are selectively placed in any suitable site within the pharyngeal region 200 of the patient as shown in FIGS. 3 and 4. The placement of the electrodes in the pharyngeal region of the patient is based on several factors, such as the extent and type of dysphagia exhibited by the patient and, given the extent and type of dysphagia exhibited, those locations within the pharyngeal region, when subjected to electrical stimulus, have the possibility of eliciting the strongest and most complete swallow. An evaluation for swallowing ability is done on the patient to determine the extent and type of dysphagia. The critical elements in the evaluation are to determine the presence of a gag reflex, a dry swallow, and ability to tolerate one's own secretions. The placement of the electrodes may be changed several times in an effort to obtain the strongest and most effective treatment.

As shown in FIGS. 3 and 4, in one embodiment of the invention, a pair of electrodes 202 is positioned on the skin of the pharyngeal region 200 at approximately the position of the lesser horn 204 of the hyoid bone 206 on either side of the pharyngeal region 200 and just above the body of the hyoid bone 206. The electrodes overlie the muscles of the floor of the mouth (not shown).

In a second embodiment of the present invention, a pair of electrodes 208 is positioned on the skin of the pharyngeal region 200 on one side of the midline of the pharyngeal region 200. One electrode 208a is placed on the thyrohyoid membrane 210 at approximately the level of the lesser horn 204 close to the hyoid bone 206. This electrode 208a overlies the sternothyroid muscle 212 and the thyrohyoid muscle 214. The other electrode 208b is placed on the cricoid cartilage 216 to the side of the midline of the pharyngeal region 200. This electrode overlies the sternohyoid muscle 218 and the sternothyroid muscle 212 on one side of the midline of the pharyngeal region.

In a third embodiment of the present invention, a pair of electrodes 220 is positioned on the skin of the pharyngeal region 200 on the thyrohyoid membrane 210 on either side of the midline of the pharyngeal region 200. These electrodes overlie the thyrohyoid muscle 214 and the sternohyoid muscle 218.

In a fourth embodiment of the present invention, a pair of electrodes 222 is positioned on the skin of the pharyngeal region 200 on either side of the midline of the pharyngeal region 200 proximately midway between the thyroid notch 224 and the cricoid cartilage 216. These electrodes overlie the sternohyoid muscle 218 and the transition zone between the sternothyroid muscle 212 and the thyrohyoid muscle 214 on either side of the midline of the pharyngeal region 200.

In a fifth embodiment of the present invention, a pair of electrodes 226 is positioned on the skin of the pharyngeal region 200 on one side of the midline of the pharyngeal region 200. One electrode 226a is placed just lateral to the lesser horn 204 of the hyoid bone 206 proximately midway between the hyoid bone 206 and the lower border of the mandible (not shown). This electrode overlies the mylohyoid muscle 228 and the digastric muscle 230. The other electrode 226b is placed proximate to the upper end of the thyrohyoid membrane 210 and proximate to the hyoid bone 206 or on the hyoid bone 206 proximately at the level of the lesser horn 204 of the hyoid bone 206. This electrode overlies the sternothyroid muscle 212 and the thyrohyoid muscle 214.

In a sixth embodiment of the present invention, a pair of electrodes 232 is positioned on the skin of the pharyngeal region 200 to the side of the midline of the pharyngeal region 200. One electrode 232a is placed on the midline of the pharyngeal region near the chin (not shown). The other electrode 232b is placed laterally to the other electrode. These electrodes overlie the mylohyoid muscle 228 and the digastric muscle 230 in the midline and to one side of the midline of the pharyngeal region 200.

EXAMPLE 1

Ninety four patients suffering from dysphagia as a result of a stroke or neurodegeneration were studied. The swallowing ability of each patient was evaluated to determine the extent and type of dysphagia exhibited by the patient. The swallowing ability of each patient was assigned a number which corresponds to a defined swallow state wherein the swallow states are listed below: swallow state zero is the inability to have a pharyngeal contraction; swallow state one is the ability to swallow one's own secretions; swallow state two is the ability to swallow paste, pudding, or similar substances; swallow state three is the ability to swallow honey or similar substances; swallow state four is the ability to swallow nectar or similar substances; swallow state five is the ability to swallow thin liquids; and swallow state six is the ability to swallow water. All of the patients were determined to have swallowing states of either zero or one, indicating the patient did not have a complete pharyngeal contraction and had no gag reflex or the ability to handle secretions. The patients were then subjected to a series of treatment sessions. The patients were divided into two treatment groups: electrical stimulation and thermal stimulation.

Sixty three patients were subjected to a series of electrical stimulation treatment sessions. Preferably, the patients were subjected to a least seven electrical stimulation treatment sessions. In each treatment session, electrodes were selectively placed on the skin of the pharyngeal region of the patient. The placement of the electrodes was determined by the extent and type of dysphagia exhibited by the patient and, given the extent and type of dysphagia exhibited, those locations within the pharyngeal region, when subjected to electrical stimulus, have the possibility of eliciting the strongest and most complete swallow. Electrode placement was adjusted until the patient achieved the most complete swallowing contraction for which he was capable. Once the correct electrode placement was determined, the intensity of the current was increased by small increments until the tolerance and comfort level limits are reached in the patient. The optimal intensity was realized when the patient felt a tugging or pinch in the area of stimulation. The patient was then subjected to continuous electrical stimulation wherein electric pulses were continuously generated and delivered to the electrodes until a complete swallow is achieved or the tolerance level was reached in the patient. This step was repeated five to twenty times in each treatment session wherein the patient was subjected to continuous electrical stimulation. If the electrical stimulation was successful in promoting a complete contraction, swabbing of the oral cavity was done and the patient attempted a dry swallow. In those patients who did not exhibit any pharyngeal contraction, one or more treatment sessions were required before an adequate dry swallow occurred.

Once an adequate dry swallow was achieved, oral intake was provided to assist in the treatment. The consistency of the oral intake is determined by the strength of the contraction elicited by the patient. If the patient was able to swallow his own saliva, swabbing the oral cavity with a sponge moistened by water or juice was performed. The patient attempted to swallow the water or juice while subjected to continuous electrical stimulation. Once the patient had achieved audible, strong contractions, the patient was challenged with pudding, thick liquid, or ice slush. The patient attempted to swallow these substances while subjected to continuous electrical stimulation. Once three to five strong swallows were achieved with the assistance of electrical stimulation, the patient attempted to swallow these substances without the assistance of electrical stimulation. Treatment sessions continued with each patient until the patient's improvement plateaus.

Thirty-one patients were subjected to a series of thermal stimulation treatment sessions. Preferably, the patients were subjected to a least seven thermal stimulation treatment sessions. In each treatment session, a mirror or probe was immersed in ice or cold substance. The tonsillar fossa was stimulated with the mirror or probe. The patient then closed his mouth and attempted a dry swallow. If the stimulation was successful in promoting a complete contraction, oral intake was provided to assist in the treatment. The consistency of the oral intake is determined by the strength of the contraction elicited by the patient. Once an adequate dry swallow was achieved, oral intake was provided to assist in the treatment. The consistency of the oral intake is determined by the strength of the contraction elicited by the patient. If the patient was able to swallow his own saliva, swabbing the oral cavity with a sponge moistened by water or juice was performed. The patient attempted to swallow the water or juice while subjected to thermal stimulation. Once the patient had achieved audible, strong contractions, the patient was challenged with pudding, thick liquid, or ice slush. The patient attempted to swallow these substances while subjected to thermal stimulation. Once three to five strong swallows were achieved with the assistance of thermal stimulation, the patient attempted to swallow these substances without the assistance of thermal stimulation. Treatment sessions continued with each patient until the patient's improvement plateaus. Once the patient had achieved audible, strong contractions, the patient was challenged with pudding, thick liquid, or ice slush. The patient attempted to swallow these substances while subjected to continuous electrical stimulation. Once three to five strong swallows were achieved with the assistance of electrical stimulation, the patient attempted to swallow these substances without the assistance of thermal stimulation. Treatment sessions continued with each patient until the patient's improvement plateaus.

Figure 5:
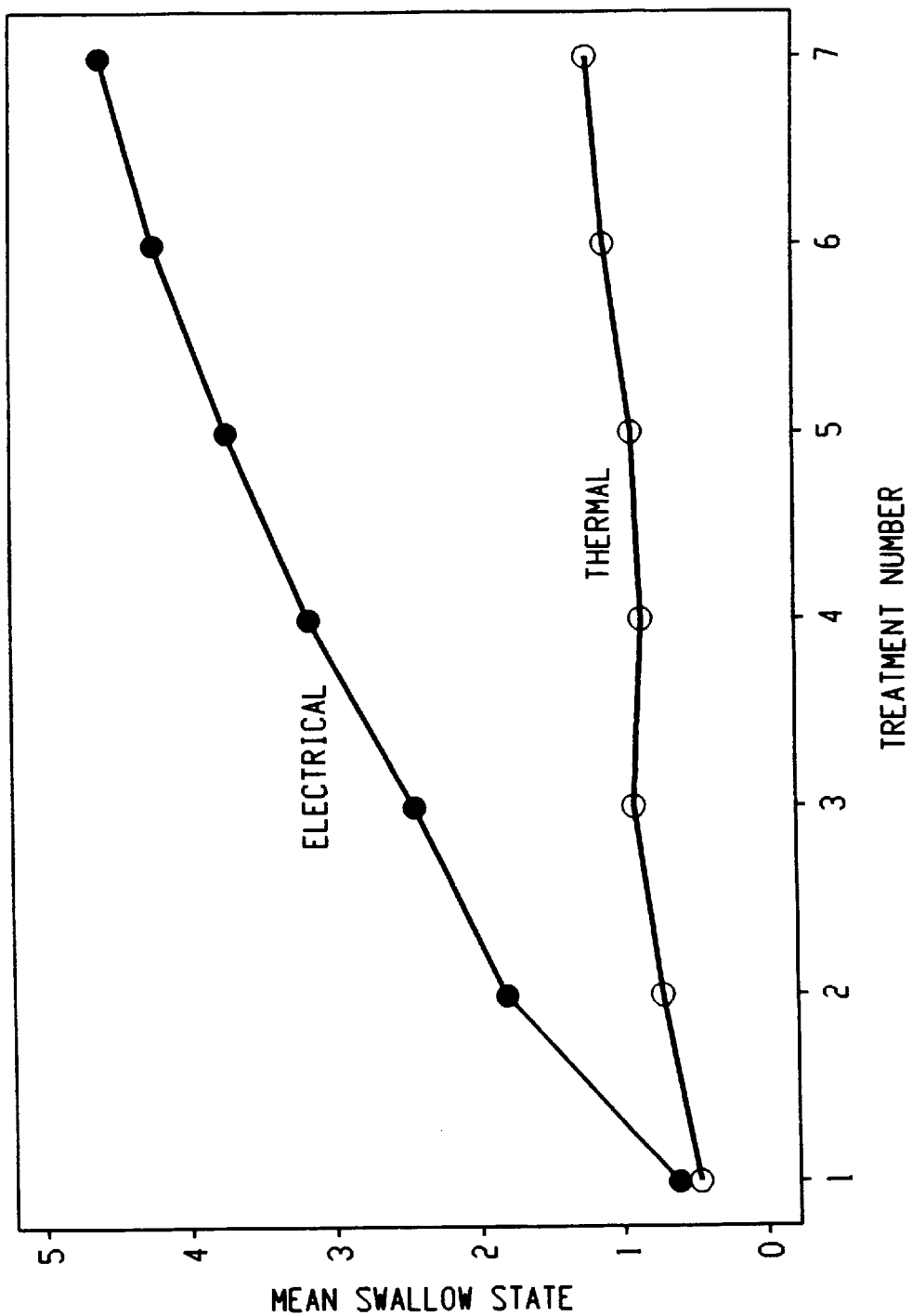
FIG. 5 is a graph illustrating the effectiveness of electric pharyngeal neuromuscular stimulation method and device according to the present invention.

The effectiveness of the electrical stimulation treatments and the thermal stimulation treatments is shown in FIG. 5. FIG. 5 is a graph illustrating the mean swallowing state achieved after electrical stimulation treatment sessions and thermal stimulation treatments. After seven treatment sessions, the mean swallowing state of the patients treated with electrical stimulation was swallow state five or the ability to swallow thin liquids. After seven treatment sessions, the mean swallowing state of the patients treated with thermal stimulation was only swallow state one or the ability to handle one's own secretions.

The method and device for electrical pharyngeal neuromuscular stimulation of the present invention provides an effective and non-invasive treatment for dysphagia. The method and device for electrical pharyngeal neuromuscular stimulation is more effective for treating dysphagia than traditional treatment methods, such as thermal stimulation. Further, the method and device of the present invention is effective for treating worst-case dysphagia resulting from neurodegeneration and strokes.

While various embodiments of a method and device for artificially promoting a swallowing reflex have been disclosed, it should be understood that modifications and adaptions thereof will occur to persons skilled in the art. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

Having thus described the invention, it is claimed:

1. A method for electrical pharyngeal neuromuscular stimulation for artificially promoting swallowing, said method comprising the steps of:

selectively placing a plurality of electrodes in electrical contact with tissue of a pharyngeal region of an associated animal;

generating a series of electrical pulses using a generator including a pulse rate modulator for generating said series of electrical pulses at a predetermined frequency, a pulse width modulator for modulating each of said series of electrical pulses to have a predetermined duration, a circuit for regulating a voltage of said series of electrical pulses to prevent said voltage from exceeding a predetermined voltage limit, and a circuit for regulating a current of said series of electrical pulses to prevent said current from exceeding a predetermined current limit; and providing said series of electrical pulses to said plurality of electrodes.

* * * * *